United States Patent [19]

Schlingmann et al.

[11] Patent Number: 5,747,304
[45] Date of Patent: May 5, 1998

[54] **FUNGICIDAL AGENTS LL-15G256γ,δ, AND ε PRODUCED BY LL-15G256 (*HYPOXYLON OCEANICUM*)**

[75] Inventors: Gerhard Schlingmann, Hillburn, N.Y.; Lisa Milne, Haddonfield, N.J.; Cedric J. Pearce, Chapel Hill, N.C.; E. B. Gareth Jones, Portsmouth Polytechnic, United Kingdom; David A. Albaugh, Trenton, N.J.

[73] Assignee: American Cyanamid Company, Madison, N.J.

[21] Appl. No.: 460,331

[22] Filed: Jun. 2, 1995

[51] Int. Cl.$^6$ .............. C12P 17/10; C12P 21/04; A61K 38/06; C07K 5/00
[52] U.S. Cl. .............. 435/121; 435/71.1; 435/171; 435/254.1; 514/11; 514/21; 530/317; 530/331; 530/332
[58] Field of Search .............. 514/11, 21; 530/317, 530/331, 332; 435/71.1, 254.1, 121, 171

[56] References Cited

PUBLICATIONS

"Formulation and Regeneration of Protoplasts Dervied from a Temperature–Sensitive Osmotic Strain of *Neurospora crass*", Selitrennikoff et al, Expt. Mycology, 5, pp. 155–161 (1981).

"Use of a Temperature–Sensitive, Protoplast–Forming *Neurospora crassa* Strain for the Detection of anitfungal Antibiotics", Selitrennikoff, Antimicrobial Agents and Chemotherapy, 23, pp. 757–765 (1983).

"A Modified Screen for the Detection of Cell Wall–Acting Antifungal Compounds", Kirsch et al, The Journal of Antibiotics, 39, pp. 1620–1622 (1986).

"Hypoxylon Oceanicum SP. Nov. from Mangroves", Schatz, Mycotaxon, XXXIII, pp. 413–418 (1988).

"Mechanism–Based Screening for the Discovery of Novel Antifungals", D. Kirsch et al, pp. 177–221 in The Discovery of Natural Products with Therapeutic Potential, V. Gullo, Ed., Butterworth–Heinemann, Boston, MA (1993).

*Primary Examiner*—Leon B. Lankford, Jr.
*Assistant Examiner*—Christopher R. Tate
*Attorney, Agent, or Firm*—Charles F. Costello, Jr.

[57] ABSTRACT

This invention provides new antifungal compounds of Formula I or II:

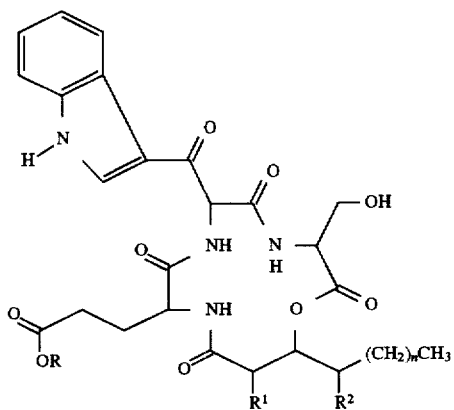

Formula I

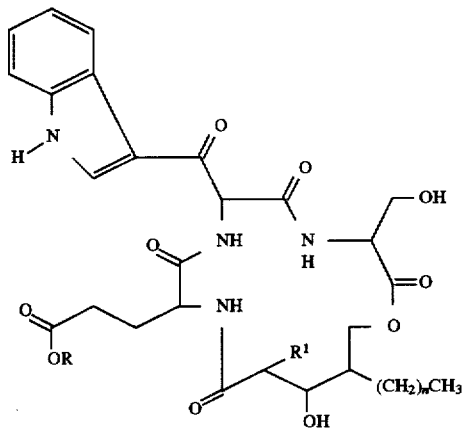

Formula II wherein R, $R^1$ and $R^2$ are defined in the specification produced by culture LL-15G256 (*Hypoxylon oceanicum*), NRRL 21363 and their production by fermentation and use as antifungal agents.

14 Claims, 4 Drawing Sheets

FUNGICIDAL AGENTS LL-15G256γ,δ, AND ε PRODUCED BY LL-15G256 (HYPOXYLON OCEANICUM)

BACKGROUND OF THE INVENTION

This invention relates to new antifungal compounds produced by culture LL-15G256 (*Hypoxylon oceanicum*), NRRL 21363, to their production by fermentation. Isolation and purification of the active components produced by the culture has yielded antifungal compounds designated LL-15G256γ, LL-15G256δ, LL15G256ε as well as other minor components.

SUMMARY OF THE INVENTION

The invention provides to the art novel antifungal compounds of Formula I and II:

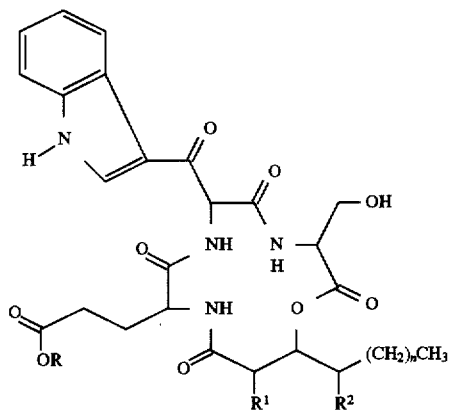

Formula I

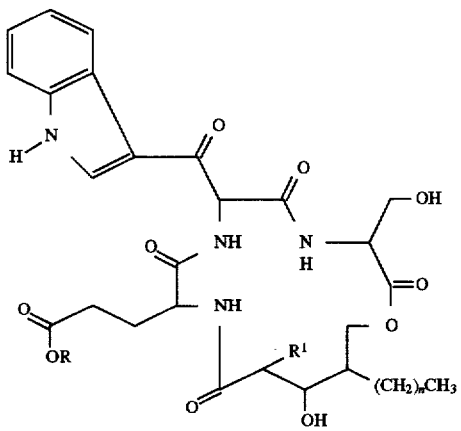

Formula II wherein n is 3 to 10;

R is hydrogen, $C_1$–$C_4$ alkyl or a pharmaceutically acceptable salt cation selected from the group consisting of sodium, potassium, calcium, lithium, magnesium, ammonium and tetra($C_1$–$C_4$)alkyl ammonium;

$R^1$ is hydrogen or methyl; and $R^2$ is hydrogen or methyl.

This invention also provides a process for producing the antifungal compounds of Formula I and II by aerobically fermenting the fungus LL-15G256, NRRL 21363; a biologically pure culture of the fungus LL 15G256, NRRL 21363; composition containing the compounds of Formula I and II, and methods for the protection of plants from plant pathogenic fungi.

DESCRIPTION OF THE PREFERRED EMBODIMENTS

Of particular interest are four depsipeptides designated LL-15G256g, LL-15G256d, LL-15G256e and LL-15G256g methyl ester having the following physico-chemical characteristics:

LL-15G256γ (gamma)

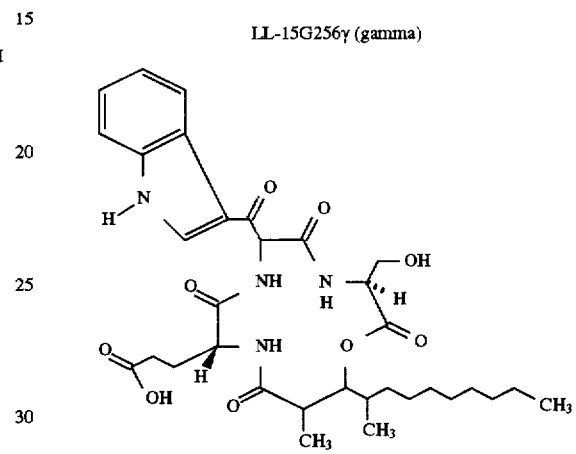

a) Apparent Molecular Formula: $C_{33}H_{46}N_4O_9$;

b) Molecular Weight: MS(FAB)=m/z 643 (M+H)$^+$

HRMS calc'd for $C_{33}H_{46}N_4O_9$=m/z 643.3343

Figure 1:
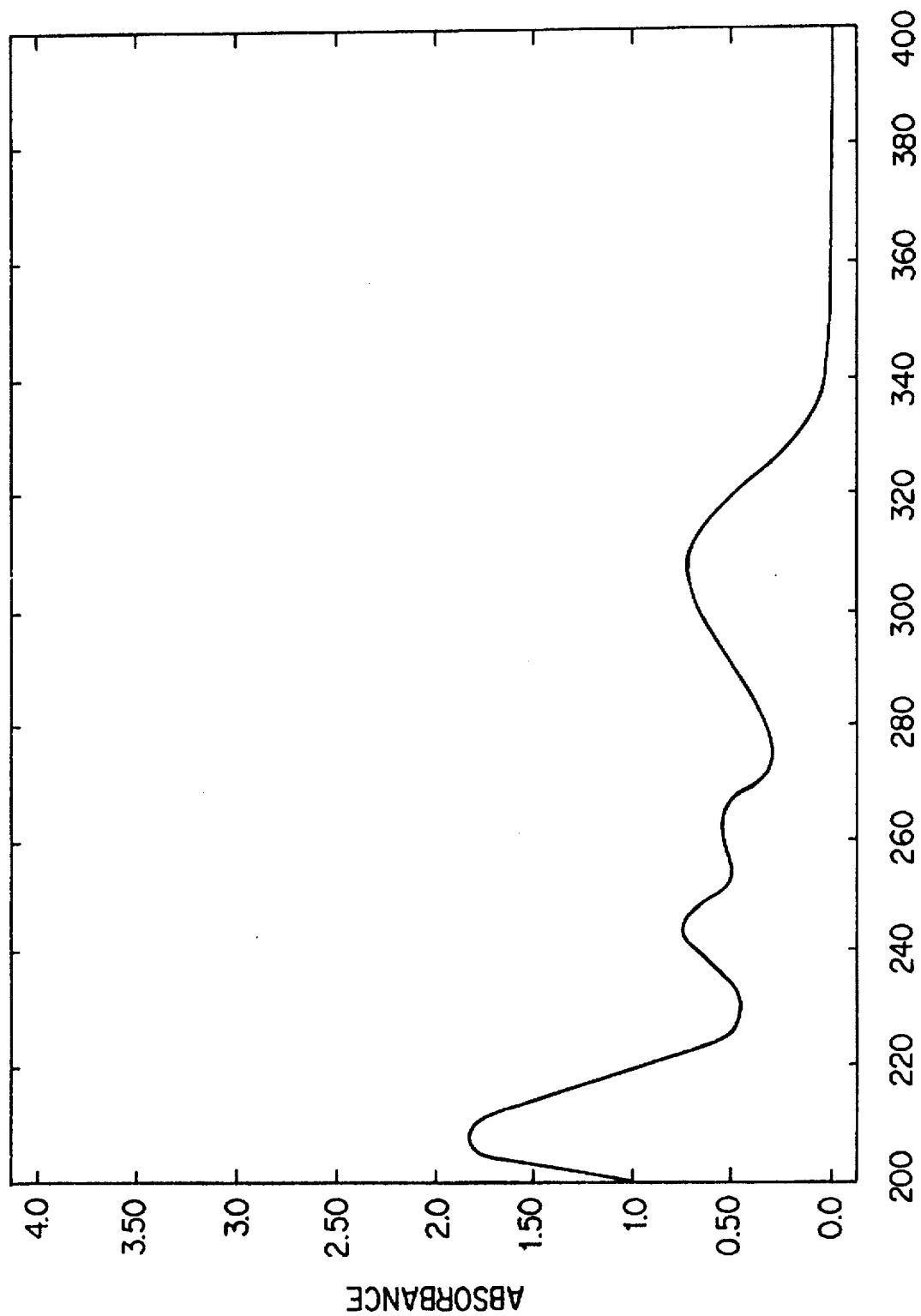
FIG. 1: Ultraviolet absorption spectrum for LL-15G256g, LL-15G256d, and LL15G256e.
Figure 2:
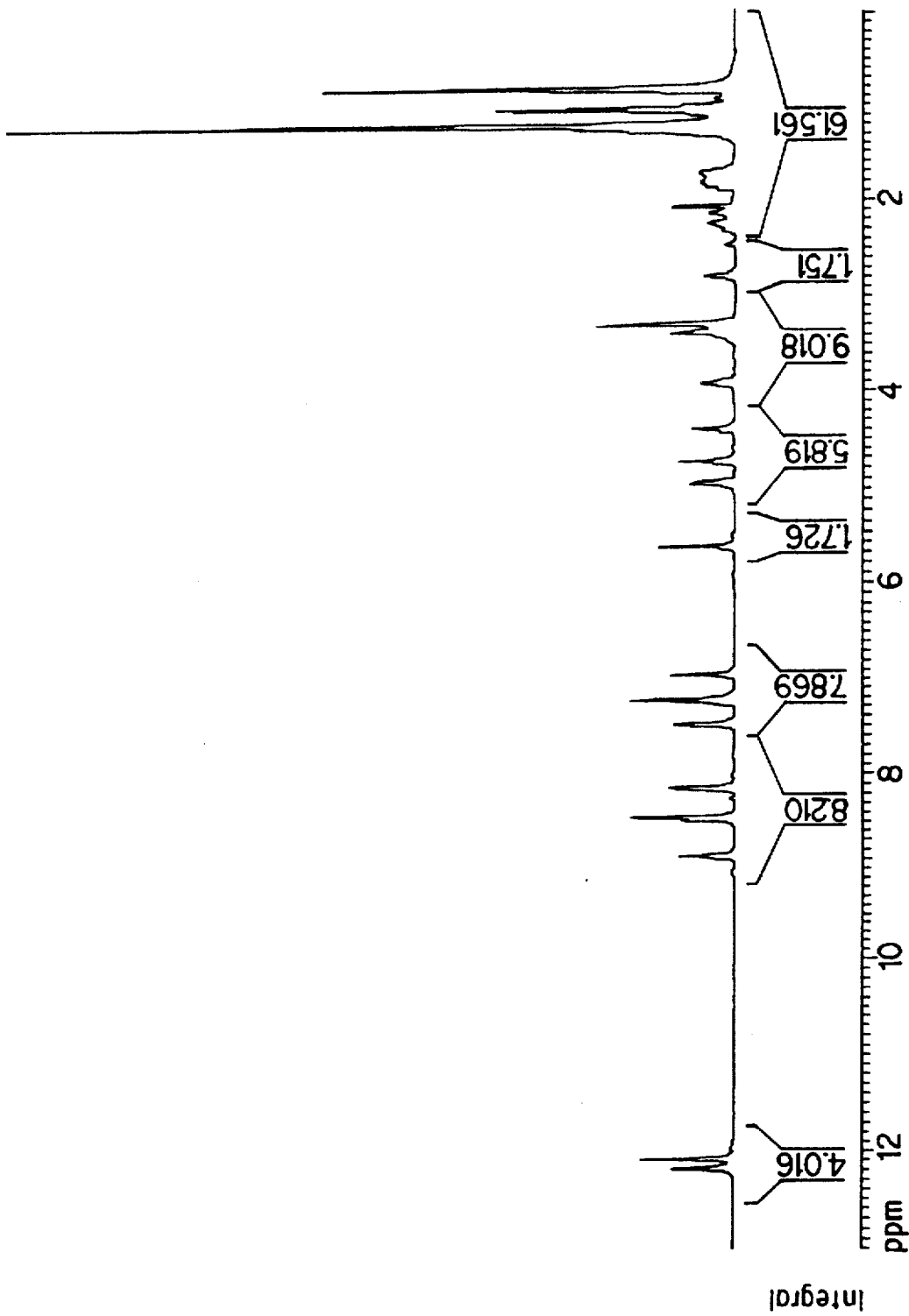
FIG. 2: $^1$H NMR spectrum for LL-15G256g.

HRMS observed=m/z 643.3349; Δmmu=0.6;

c) Specific Rotation: $[\alpha]^D_{25}$=+22.9±1, (c=1.07%, MeOH);

d) Ultraviolet Absorption Spectrum: as shown in FIG. 1; λmax nm (ε) (MeOH)=206(41,710), 245(16,820), 264(12,275), 307(16,100);

e) Infrared Absorption Spectrum: 3335, 3121, 2957, 2927 (s), 2855(s), 1723(s), 1681(s), 1664(s), 1645(s), 1534, 1518 (s), 1459, 1430, 1376(s), 1319, 1266, 1245, 1227, 1194, 1115, 748 cm$^{-1}$;

f) Proton Magnetic Resonance Spectrum: as shown in FIG. 2 (300 MHz, d$_6$-DMSO)

g) Carbon-13 Nuclear Magnetic Resonance Spectrum: (300 MHz, d$_6$-DMSO, ppm downfield from TMS), significant peaks are listed below:

| | | | |
|---|---|---|---|
| 184.9 | 174.9 | 173.5 | 171.9 |
| 169.0 | 167.4 | 136.9 | 136.6 |
| 125.5 | 123.3 | 122.4 | 121.1 |
| 113.4 | 112.4 | 78.39 | 62.04 |
| 58.83 | 54.92 | 51.89 | 41.21 |
| 33.36 | 33.15 | 31.23 | 29.93 |
| 29.14 | 28.96 | 28.64 | 26.67 |
| 24.91 | 22.04 | 16.08 | 13.89 |
| 13.42 | | | | h) Analysis calc'd for $C_{33}H_{46}N_4O_9$;

Theory C=61.68; H=7.17; N=8.72

Found C=61.70; H=7.83; N=7.37

15G256d (delta)

Figure 3:
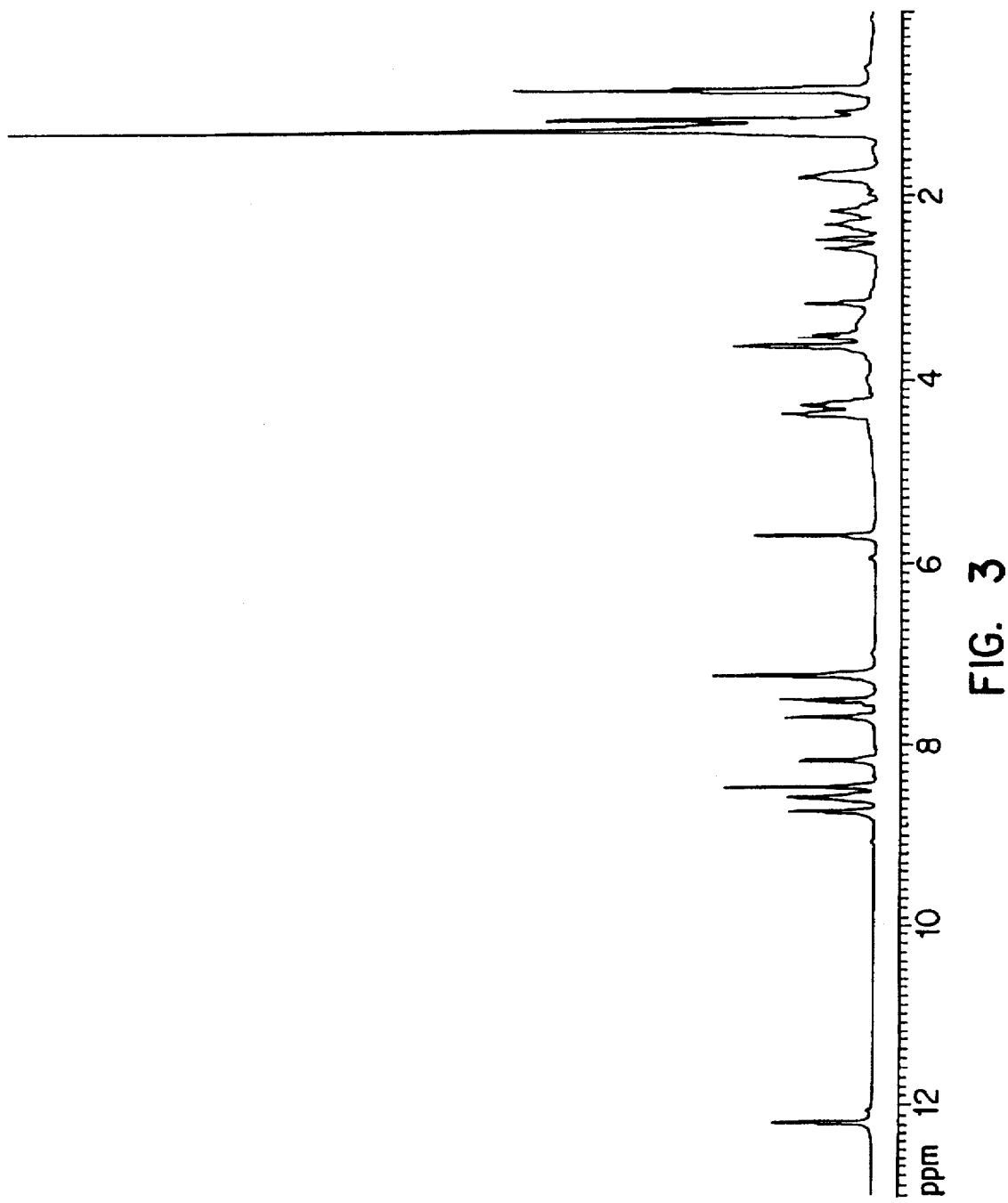
FIG. 3: $^1$H NMR spectrum for LL-15G256d.

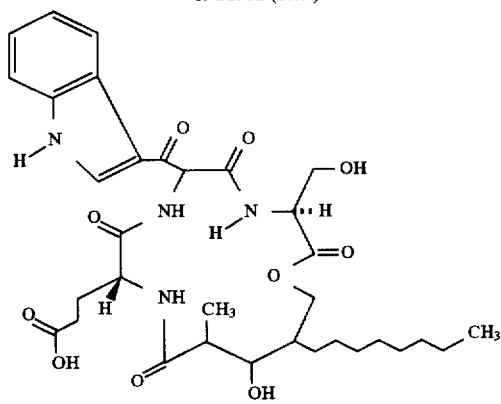

a) Apparent Molecular Formula: $C_{33}H_{46}N_4O_{10}$;
b) Molecular Weight:
MS(FAB)=m/z 659.3 $(M+H)^+$;
MS(FAB)=m/z 681.3 $(M+Na)^+$
HRMS calc'd for $C_{33}H_{46}N_4O_{10}Na$=m/z 681.3112
HRMS observed=m/z 681.3119;
ΔEmmu=−0.7 mmu;

c) Ultraviolet Absorption Spectrum: as shown in FIG. 1; λmax nm (ε) MeOH=206(33,720), 246(13,600), 262(9.925), 310(13,100);

d) Proton Magnetic Resonance Spectrum: as shown in FIG. 3 (300 MHz, $d_6$-DMSO);

e) Carbon-13 Nuclear Magnetic Resonance Spectrum: (300 MHz, $d_6$-DMSO, ppm downfield from TMS), significant peaks are listed below:

| | | | |
|---|---|---|---|
| 185.9 | 177.0 | 173.6 | 172.0 |
| 169.2 | 166.8 | 137.1 | 136.6 |
| 125.6 | 123.2 | 122.2 | 121.1 |
| 114.2 | 112.4 | 76.16 | 64.97 |
| 61.78 | 60.35 | 54.55 | 52.76 |
| 41.21 | 40.93 | 31.26 | 30.61 |
| 30.10 | 29.46 | 28.97 | 28.70 |
| 26.34 | 25.59 | 22.05 | 15.51 |
| 13.90 | | | |

15G256ε (epsilon)

Figure 4:
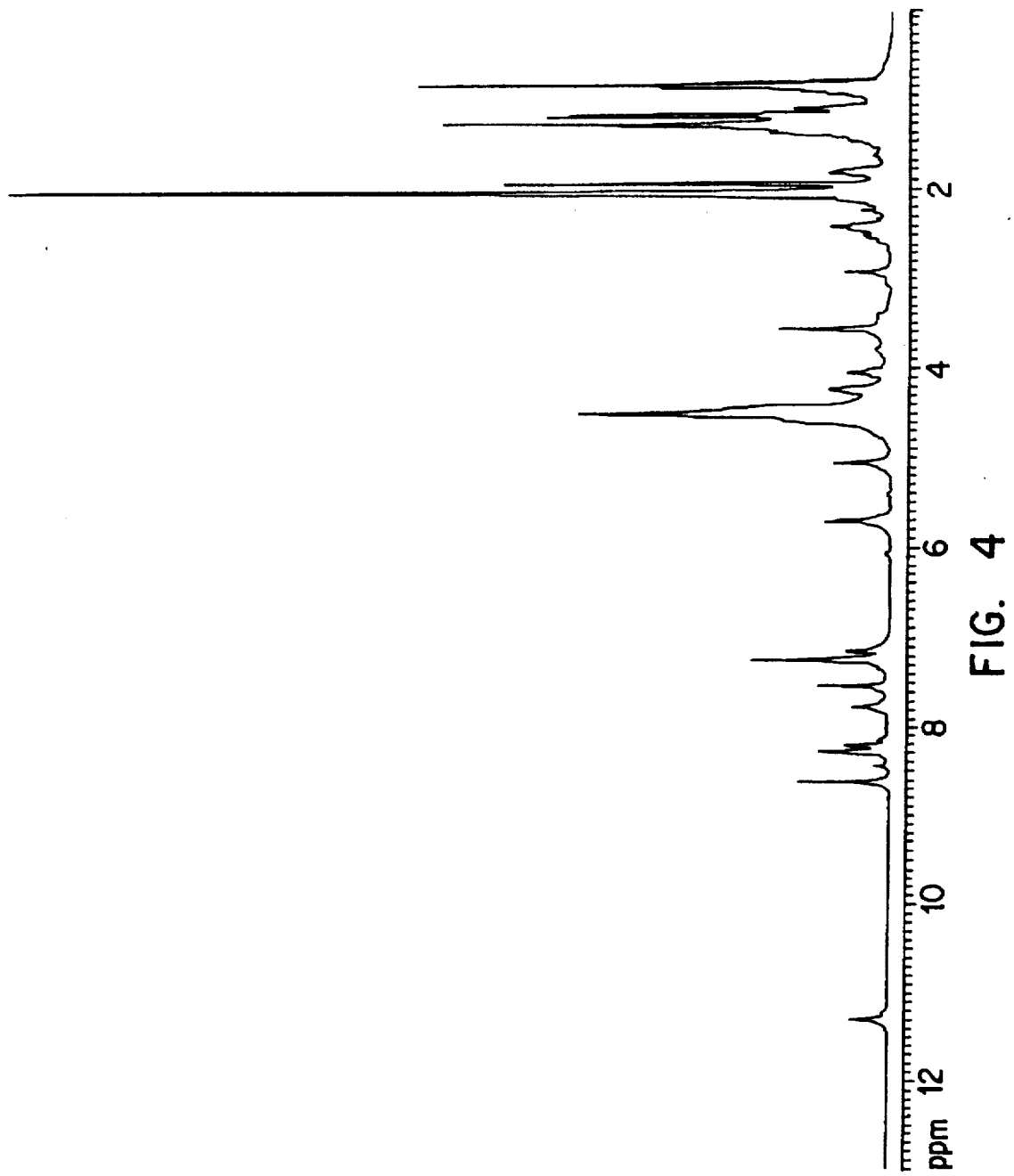
FIG. 4: $^1$H NMR spectrum for LL-15G256e.

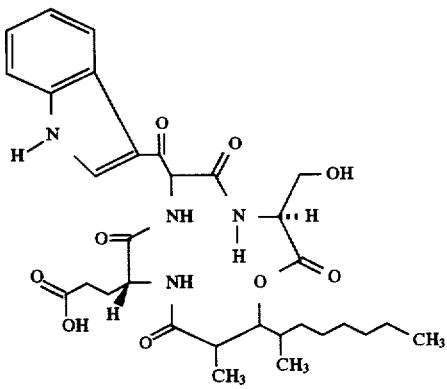

a) Apparent Molecular Weight: $C_{31}H_{42}N_4O_9$;
b) Molecular Weight:
MS(FAB)=m/z 615.2 $(M+H)^+$
MS(FAB)=m/z 637.3 $(M+Na)^+$
HRMS calc'd for $C_{33}H_{46}N_4O_9Na$=m/z 637.2849
HRMS observed=m/z 637.2840;
Δmmu=+0.9mmu;

c) Ultraviolet Absorption Spectrum: as shown in FIG. 1; λmax nm (ε) MeOH=206(33,720), 246(13,600), 262(9.925), 310(13,100);

d) Infrared Absorption Spectrum: 3350, 3121, 2956(s), 2928(s), 1645(s), 1518(s), 1455, 1432, 1375(s), 1339, 1316, 1245, 1192 $cm^{-1}$;

e) Proton Magnetic Resonance Spectrum: as shown in FIG. 4 (300 MHz, $d_6$-acetone);

f) Carbon-13 Nuclear Magnetic Resonance Spectrum: (300 MHz, $d_6$-acetone, ppm downfield from TMS), significant peaks are listed below:

| | | | |
|---|---|---|---|
| 185.3 | 176.4 | 174.0 | 172.1 |
| 170.3 | 168.4 | 138.0 | 137.8 |
| 127.0 | 124.4 | 123.4 | 122.6 |
| 114.8 | 113.1 | 79.95 | 63.25 |
| 61.23 | 55.89 | 53.81 | 43.13 |
| 35.14 | 34.56 | 32.55 | 30.40 |
| 30.15 | 27.89 | 25.99 | 23.27 |
| 16.77 | 14.30 | 14.08 | |

LL-15G256γ (gamma) methyl ester

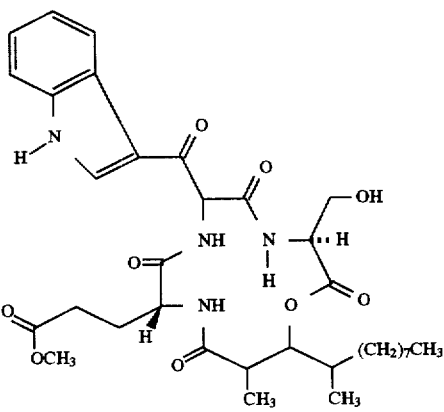

a) Apparent Molecular Formula: $C_{34}H_{48}N_4O_9$;

b) Ultraviolet Absorption Spectrum: λmax nm (ε) (MeOH) =206(33,720), 246(13,600), 262(9,925), 310(13,100);

c) Carbon-13 Nuclear Magnetic Resonance Spectrum: (300 MHz, $d_6$-acetonitrile, ppm downfield from TMS), significant peaks are listed below:

| | | | |
|---|---|---|---|
| 185.6 | 176.6 | 174.1 | 172.4 |
| 170.6 | 168.6 | 138.1 | 137.8 |
| 126.9 | 124.9 | 123.9 | 122.6 |
| 114.8 | 113.4 | 80.8 | 63.4 |
| 61.6 | 55.7 | 54.3 | 52.3 |
| 43.3 | 35.7 | 34.5 | 32.7 |
| 30.9 | 30.6 | 30.4 | 30.1 |
| 27.9 | 26.0 | 23.4 | 17.0 |
| 14.43 | 14.38 | | |

These compounds are a novel class of depsipeptides containing a branched chain beta-hydroxy fatty acid residue and a beta-keto tryptophan moiety as distinguishing features.

The antifungal compounds LL-15G256g, LL-15G256d, and LL-15G256e, as well as other minor components, are produced by aerobic fermentation of LL-15G256 (*Hypoxylon oceanicum*), originally isolated from mangrove wood from Shenzen, China.

It will be appreciated by those skilled in the art that the present invention includes within its scope the novel antifungal compounds of Formula I and II as well as any other minor components produced. Such compounds may be obtained in dilute form, as crude concentrates, as a complex of all components or in pure form as individual components.

Culture LL-15G256 has been taxonomically characterized on the basis of teleomorph morphology as a strain of *Hypoxylon oceanicum* Schatz (Schatz, Mycotoxon, 33:413, 1988). A culture of LL-15G256 is maintained in the culture collection of the Medical Research Division, American Cyanamid Company, Pearl River, New York. A viable culture of this new microorganism has been deposited on Dec. 13, 1994 in the Agricultural Research Service Culture Collection Laboratory, Northern Regional Research Center, U.S. 1815 North University Street, Peoria, Ill. 61604 and has been added to its permanent collection. It has been assigned the strain designation NRRL 21363 by such depository. The fungus has been deposited under the Budapest Treaty.

Colonies of this culture growing on oatmeal agar cover the medium surface in the Petri dish in 4 weeks. Growth is at first white, velvety, appressed, irregularly zonate, with dense, entire margins, then darkening on the zonation lines. The reverse side of the culture dish is uncolored.

On decorticated wood, stromata of this culture are superficially seated, occasionally embedded at the base, pulvinate to hemispherical, 0.4–0.8 mm in diameter, single or several coalesced, linear to suborbicular, surface carbonaceous, interior leathery. When young, stromata is covered with a whitish hyphal layer, at maturity, black perithecial projections generally inconspicuous, porus prominent with perithecia subglobose, 0.4–0.6 mm in diameter are observed. Asci are 8-sored, 177–219 mm sp. p. 112–140 mm, stipe 37–79 mm, apical apparatus dark blue in Meizer's reagent, tapering cylindrical with distinct apical rim, (4.7–)5.6–6.6×4.2–4.7 mm, ascospore uniseriated to obliquely uniseriate or partially biseriate at the upper end of the ascus. Ascospores are grey-olive to opaque brown, more or less inequilaterally ellipsoid, vental side varying in degree of convex curvature, upper end broadly rounded, lower end slightly pointed, (17.9–) 18.8–21.6(–22.6)×8.5–9.9 mm (av. 20.7×9.3 mm, n/20), biguttulate. Ascospore wall is smooth and relatively thick, without appendages or loosening epispore, germination slit usually clearly seen on the dorsal side straight, conspicuous, ½–¾ total length of spore, paraphyses long thread-like, remotely septate with droplets.

It is to be understood that for the production of the new antifungal compounds LL-15G256γ, LL-15G256δ, and LL15G256ε, the present invention is not limited to this particular organism or to organisms fully answering the above growth and microscopic characteristics, which are given for illustrative purposes only. In fact it is desired and intended to include the use of mutants produced from this organism by various means such as exposure to x-ray radiation, ultraviolet radiation, N'-methyl-N-nitrosoguanidine and the like.

BIOLOGICAL ACTIVITY

LL-15G256 γ and ε are tested for antifungal activity by the microbroth dilution method (Table 1). Serial dilutions of the compounds are mixed with the assay organisms in a liquid growth medium in the wells of the microtiter plate. After incubation at 28° C. for 20 hours, the wells are observed for turbidity, the absence of which indicates growth inhibition.

TABLE 1

Antifungal Activity (MIC, µg/ml)[1] of 15G256γ (gamma) and 15G256ε (epsilon)

| Organism | 15G256γ | 15G256δ |
|---|---|---|
| C. albicans 54 | >256 | >256 |
| S. cerevisiae 427 | >256 | >256 |
| U. maydis 106 | 16 | 32 |
| R. rubra 388 | 128 | 128 |
| C. neoformans 4414 | 256 | 256 |
| N. crassa (OS-1) | 256 | 256 |

[1]Microbroth dilution method, medium: YMB, inoculum: approx. 10⁴ cfu/ml, incubation 28° C. for 20 hours.

in Vivo Evaluation as Fungicidal Agents (Table 2)

Compounds are dissolved in a 50/50 (v/v) mixture of methanol and acetone, diluted to the desired concentration with water and surfactant and sprayed onto the test plants. After drying, the test plants are treated with fungal inoculum. When disease symptom development is optimal, plants are rated for disease control. Inoculated untreated plant, solvent/surfactant treated plants and plants treated with a reference standard are used for comparison.

| Test Organisms | | |
|---|---|---|
| HEADER | COMMON NAME | SCIENTIFIC NAME |
| AS | Apple scab | Venturia inaequalis |
| GDM | Grape downy mildew | Plasmopara viticola |
| PB | Pepper botrytis | Botrytis cinerea |
| RB | Rice blast | Pyricularia oryzae |
| SBC | Sugar beet cercospora | Cercospora beticola |
| TEB | Tomato early blight | Alternaria solani |
| WSN | Wheat septoria nodorum | Leptosphaeria nodurum |
| WPM | Wheat powdery mildew | Erysiphe graminis f.sp. tritici |

Compounds are rated for control of each disease according to the scale shown below:

| Rating | % Control of Disease |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

The results are reported in Table 2.

TABLE 2 in Vivo Screening Data:

DISEASE CONTROL BY TARGET

| CPD | DOSE (ppm) | AS | GDM | PB | RB | SBC | TEB | WPM | WSN |
|---|---|---|---|---|---|---|---|---|---|
| 15G256γ | 500.0 | 6 | 9 | 0 | 4 | 7 | 2 | 6 | 0 |
| | 125.0 | 3 | 6 | 5 | 0 | 6 | 2 | 0 | 0 |
| | 31.3 | 0 | 0 | 0 | 0 | 3 | 0 | 0 | 0 |

The antifungal compounds of the present invention are effective for controlling and/or preventing phytopathogenic fungi when employed in effective amounts. This will vary somewhat with the virulence of the fungus in question and with other factors such as the environment in which treatment is conducted. These compounds are especially useful for the control of fungi which are the causative agents for grape downy mildew and potato and tomato late blight. Certain compounds of the invention may not only be employed to control fungi that have infected the plants, but also may be applied to healthy plants or seeds or to the soil in which the plant is to be grown in order to prevent infestation.

To protect plants from phytopathogenic fungi, the compounds of this invention are applied to the foliage of the plant, to the seed of the plants, or to the soil in which the plant grows or is to be grown, in the form of a liquid, preferably an aqueous spray, or dust, or granular formation. Solutions or suspensions containing from about 20 ppm to about 1,000 ppm, and preferably 50 ppm to 500 ppm, of compounds of this invention are generally effective for this use.

The compounds of the invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrated, suspension concentrates, microemulsions and the like, all of which lend themselves to seed, soil, water and/or foliage applications to provide the requisite plant protection. Such formulations include the compounds of the invention admixed with inert, pharmacologically acceptable solid or liquid diluents.

For example, wettable powders, dusts, and dust concentrate formulations can be prepared by grinding and blending together about 25% to about 85% by weight of the compound of this invention and about 75% to about 15% by weight of a solid diluent such as bentonite, diatomaceous earth, kaolin, attapulgite, or the like, 1% to 5% by weight of a dispersing agent such as sodium lignosulfonate, and about 1% to 5% by weight of a nonionic surfactant, such as octylphenoxy ethanol, nonylphenoxy polyethoxy ethanol or the like.

A typical flowable liquid can be prepared by admixing about 30% to 90% by weight of the active ingredient with about 1% to 3% by weight of a gelling agent such as bentonite, 2% to 5% by weight of a dispersing agent such as sodium lignosulfonate, about 1% by weight of polyethyleneglycol, and about 40% to 60% by weight of water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

Application of the material is made by adding a predetermined quantity of formulated product, such as described above, to the desired volume of water or other suitable solvent, alone or in combination with other agronomic chemicals for simultaneous use.

It is understood that the compounds of the present invention can be applied singly or in combination with one or more other fungicidal compounds, such application being made either in combination of the fungicidal compounds or their formulations in a common container prior to use or by sequential application of the active fungicidal compounds or their formulations to the host crop or its environment. Compounds which may be combined with the compounds of this invention are include by but not limited to, the following: 4,6-dinitro-o-cresol, benalaxyl, benomyl, captafol, captan, carbendazim, chlorothalonil, copper, cymoxanil, dichlobutrazole, dichlofluanid, diethofencarb, difenconazole, dimethomorph, diniconazole, dinocap, dithianon, fenarimol, fentin acetate, ferbam, flusilazole, folpet, fosetyl, hexaconazole, imazalil, iprodione, mancopper, mancozeb, maneb, mepronil, mercuric oxide, metalaxyl, metiram, myclobutanil, muarinol, ofurace, oxadixyl, penconazole, pencyuron, phosphorous acid, procymidone, propineb, pyrifenox, quintozene, sodium arsenite, sulphur, thiabendazole, thophanate methyl, thiram, tolclophos-methyl, triadimefon, triadimenol, triforine, vinclozolin, zineb, and/or ziram.

GENERAL FERMENTATION CONDITIONS

Cultivation of fungal culture LL-15G256 may be carried out in a wide variety of solid and liquid culture media. Media which are useful for the production of antibiotic include an assimilable source of carbon, such as potato starch, dextrose, maltose, malt extract, etc., and an assimilable source of nitrogen such as peptone or potato or malt extract. Inorganic elements are supplied from the complex vegetable or animal extracts used in the media preparation. Aeration is supplied either by agitation in flask or by forcing air through the fermentation. Further agitation is provided by a mechanical impeller. An antifoam agent such as silicon oil may be added as needed.

GENERAL PROCEDURE FOR THE ISOLATION OF LL-15G256

Recovery of the LL-15G256 antifungal agents from fermentation broth is accomplished by extraction of the whole broth with an immiscible organic solvent such as butanol or ethyl acetate, separation of the phases and isolating the 15G256 component from the organic phase.

Alternatively, the LL-15G256 antifungal agents can be obtained from the whole broth by first adding half the fermentation volume of a suitable, water miscible solvent, such as methyl alcohol or acetonitrile, thereafter removing any solid material by filtration, then diluting the obtained filtrate with water to twice its volume and passing the liquid over a resin such as HP-20 or XAD-2 to adsorb the antifungal compounds. The LL-15G256 components are eluted from the resin by adding an organic solvent, such as methyl alcohol, acetone or acetonitrile. The crude product obtained by the above extractions represents a complex of LL-15G256 antifungal agents from which single compounds can be separated by chromatography. Purification of the individual components is accomplished by a succession of liquid chromatographic steps on silica gel and/or reverse phase resins with a variety of elution conditions.

The invention will be further described in conjunction with the following non-limiting examples.

EXAMPLE 1

Inoculum Preparation

The culture is maintained on a slant of corn meal/sea water agar, prepared by dissolving 17 g of Bacto corn meal agar in one liter of natural seawater (Carolina Biological Supply Company), adjusting the pH to 6.0 and then dispensing aliquots into suitable vessels and autoclaving for 20 minutes. Following inoculation of the slant, the culture is grown at 22° C. A plug of this culture is added to a 25×150 mm capped culture tube containing 10 mls of potato dextrose broth, prepared by adding 24 g of Difco dehydrated potato dextrose broth to 1 liter of distilled water which was then autoclaved for 20 minutes at 121° C., and two 6 mm glass beads. This tube is incubated at 22° C. with shaking at 170 rpm and a two inch throw. After a period, usually between 4–5 days, vigorous growth is observed. Ten ml of this culture is transferred to a 250 ml Erlenmeyer flask containing 50 ml of potato dextrose broth. The flask containing the broth is incubated at 22° C. with shaking at 200 rpm with a two inch throw until vigorous growth is observed, which usually occurs after 3 days of incubation.

Fermentation

Two and a half ml of the culture produced in Example 1 is tranferred to a 250 ml Erlenmeyer flask containing 50 ml of Sabaroud maltose medium, prepared by dissolving 10 g of Difco Neopeptone and 40 g of Bacto maltose in one liter of distilled water and adjusting the pH to 5.6. This mixture is incubated at 22° C. with shaking at 200 rpm with a two inch throw for 7 days.

Five Liter Scale-up Fermentation of LL-15G256

Fifty flasks are prepared as above and their contents are pooled.

EXAMPLE 2

300 Liter Scale-up Fermentation of LL-15G256
Seed Medium FM-3

| Ingredients | (%) |
| --- | --- |
| Potato-Dextrose Powder | 2.4 |
| Tap Water | 1 liter |

Production Medium FM-7P

| Ingredients | (%) |
| --- | --- |
| Maltose | 4.0 |
| Neo-peptone | 1.0 |
| CaCO$_3$ | 0.1% |
| DF40-P Antifoam | 0.3% |
| Tap Water | 1 liter |

S1 Seed Stage

One hundred ml of seed medium/500 ml flask is inoculated with frozen (−95° C.) mycelial suspension. The flask is allowed to grow for 5 days at 28° C. on a 200 rpm rotary shaker.

S2 Seed Stage

A 4 liter tank containing 3.0 liters of seed medium is inoculated with 100 ml of S2 seed growth. The tank is allowed to grow out for 3 days at 22° C. The aeration is set at 3 lpm and the agitation at 200 rpm.

S3 Seed Stage

A 41 liter tank containing 30 liters of seed medium is inoculated with 3.0 liters of S2 seed. The aeration is set at 30 lpm, the temperature is 28° C., and the agitation is 300 rpm. After 3 days growth, the seed is inoculated into the production state.

Production Stage

A 410 liter tank containing 300 liters of sterile production medium is inoculated with the contents of the S3 seed tank growth. The temperature is set at 28° C., agitation at 250 rpm, and the air flow is 250 lpm. The back pressure is initially set at 8 psi. The fermentation is allowed to proceed for 99 hours, after which time it is harvested.

EXAMPLE 3

Isolation and Purification of LL-15G256 from 5-liter Flask Fermentation

Whole mash (5L) is separated into pellet and supernatant by centrifugation at 3000 rpm for 30 minutes. The pellet is extracted with 2L of 85% aqueous acetone while the supernatant is extracted with 2L of ethyl acetate. The organic extract of the supernatant and the pellet extracts are processed separately under the following conditions. After evaporation of the solvent, the remaining solids (ca. 2 g from the pellet and ca. 1.2 g from the supernatant) are resuspended in methylene chloride and loaded onto self-packed silica gel columns (21×300 mm). The compounds are eluted with increasing concentrations of ethyl acetate (10, 25, 50, and 100%) in methylene chloride followed by a final column wash with 100% methyl alcohol. From the pellet extract six fractions are collected as indicated below.

| Fraction | Weight | Eluent Composition |
| --- | --- | --- |
| 1. | 33 mg | Methylene chloride |
| 2. | 114 mg | 10–25% EtOAc/CH$_2$Cl$_2$ |
| 3. | 423 mg | 25–50% EtOAc/CH$_2$Cl$_2$ |
| 4. | 125 mg | 50–100 EtOAc/CH2Cl2 |
| 5. | 52 mg | 100% ETOAc |
| 6. | 467 mg | 100% MeOH |

Fraction 5 contains essentially pure LL-15G256γ. Fraction 6 was further purified by reverse-phase HPLC to yield additional LL-15G256γ. The residue from fraction 6 is dissolved in 2 ml of dimethyl-sulfoxide and is loaded onto a C-8 reverse-phase HPLC column (2×50 cm). The column is eluted with a mixture of 75% methyl alcohol/water containing 0.2% trifluoro-acetic acid at a flow rate of 9.9 ml/minute. LL-15G256γ is eluted from the column between 20–25 minutes. The compound is recovered from the solvent mixture by concentration in vacuo to remove most of the methyl alcohol and then extracted with ethyl acetate. Evaporation of the ethyl acetate yields 140 mg of LL-15G256γ.

The material obtained from the silica gel chromatography of the supernatant extract is handled in a similar fashion.

EXAMPLE 4

Isolation and Purification of LL-15G256γ, LL-15G256δ, and LL-15G256ε from 300-liter Tank Fermentation Whole mash (300L) is mixed with 1.5% toluene and stirred for 30 minutes, followed by filtering through a ceramic microfilter utilizing tangential flow. The filtrate and retentate fractions are processed separately to yield the LL-15G256 compounds.

The retentate is re-slurried in methyl alcohol (100L) and filtered. The extract is concentrated in vacuo to remove the bulk of the methyl alcohol and the resulting aqueous suspension is extracted with ethyl acetate. Concentration of the ethyl acetate in vacuo yields an oily residue which on trituration with hexane (2L) results in the formation of a precipitate. The precipitate is slurried with 300 g of silica gel in 500 ml of acetone for 20 minutes. The acetone is evaporated and the resulting powder is transferred to a partially loaded silica gel column to yield a final column of 10×15 [diameter] cm. The column is eluted sequentially with 1 liter of methylene chloride, 2 liters of 50% ethyl acetate/methylene chloride, and 6 liters of ethyl acetate followed by 2L of methyl alcohol wash. The ethyl acetate fraction yields approximately 10 g of LL-15G256γ.

The filtrate is mixed with one-half volume of ethyl acetate for three hours. The ethyl acetate phase is separated and concentrated in vacuo to yield a crude mixture. To this mixture (containing precipitated material), ethyl acetate (12L) is added and the mixture is washed with water. The organic phase is concentrated in vacuo to yield an oily residue which is triturated with hexane (2L) to produce a precipitate. The precipitate is mixed with 10 g of silica gel and acetone. The residue is collected after the evaporation of acetone and charged onto a silica gel column (5 |diameter| ×10 cm) which is then eluted with a stepwise gradient (ca. 250 ml each) of ethyl acetate in methylene chloride (5, 10, 25, 50 75% and 3×100%).

Fraction 7 and 8 (100% ethyl acetate eluates) are concentrated to yield 4.5 g of solid material. The solid is dissolved in 30 ml of methyl alcohol and chromatographed in three aliquots on a $C_{18}$ column (5×30 cm) using 55% acetonitrile/0.1M trifluoroacetic acid at a flow rate of 40 ml/minute. The effluent is monitored by a variable wavelength detector at 300 nm. The fractions containing LL-15G256γ, LL-15G256δ, and LL-15G256ε eluted at 13 minutes, 15 minutes, and 30 minutes, respectively. Yield of pure components: LL-15G256γ 62 mg, LL-15G256δ 14 mg, and LL-15G256ε 2 mg.

Isolation and/or Preparation of 15G256γ-Methyl Ester

Keeping crude or purified 15G256γ as a methanolic solution slowly produces isolable quantities of 15G256γ-methyl ester which is separated from 15G256γ by reverse phase chromatography under conditions described below. This method provides 45 mg of 15G256γ-methyl ester from a reverse phase separation.

15G256γ [30 mg] is dissolved in approximately 30 ml of methyl alcohol and 4 ml of a diethyl ether/diazomethane solution is added while swirling the reaction vessel. The reaction mixture is then allowed to stand for 10 min. An HPLC analysis using an analytical Whatman $C_8$ reverse phase column eluted with 75% MeOH/10% 0.1M TFA/15% water, reveals that the original 15G256γ peak at a retention time of 4.4 min has disappeared and a single, new peak at a retention time of 6.0 min is produced instead. The reaction mixture is evaporated to dryness, redissolved in methyl alcohol, twice, and prepared for NMR analysis. The product [32 mg] is found to be 15G256γ-methyl ester.

We claim:

1. An antifungal compound of Formula I:

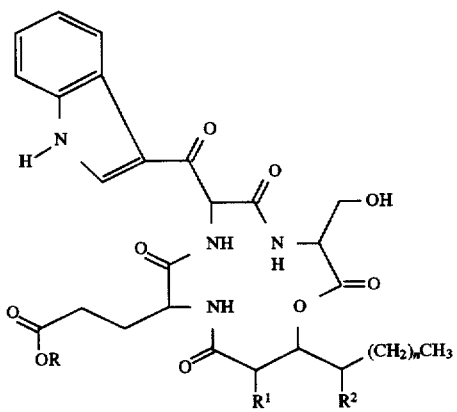

wherein n is 3 to 10;

R is hydrogen, $C_1$–$C_4$ alkyl or a pharmaceutically acceptable salt cation selected from the group consisting of sodium, potassium, calcium, lithium, magnesium, ammonium, and tetra($C_1$–$C_4$)alkyl ammonium;

$R^1$ is hydrogen or methyl; and $R^2$ is hydrogen or methyl.

2. The compound according to claim 1:

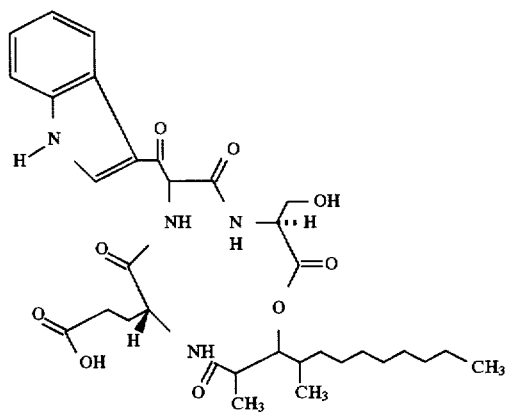

3. The compound according to claim 1:

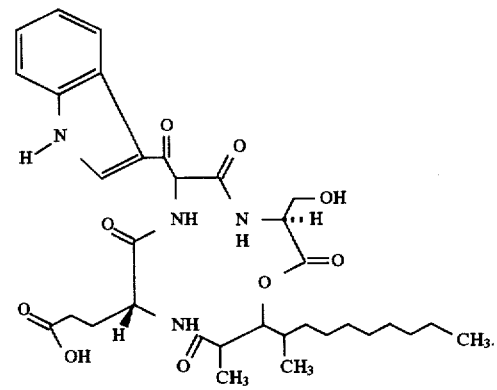

4. The compound according to claim 1:

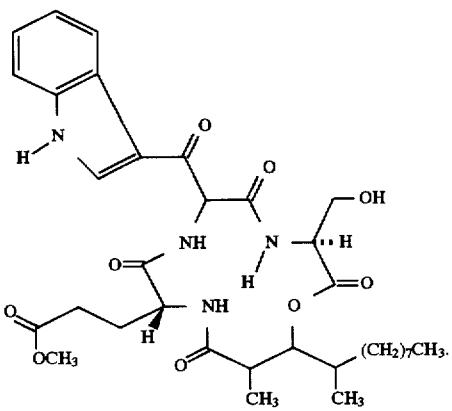

5. A method for the protection of plants from the phytopathogenic effects of plant pathogenic fungi which comprises applying to the locus of the plant or the fungi a fungicidally effective amount of the compound according to claim 1.

6. A fungicidal composition comprising an inert solid or liquid diluent and a fungicidally effective amount of the compound according to claim 1.

7. A method for the protection of plants from the phytopathogenic effects of plant pathogenic fungi which comprises applying to the locus of the plant or the fungi a fungicidally effective amount of the compound according to claim 2.

8. An antifungal compound of Formula II:

Formula II

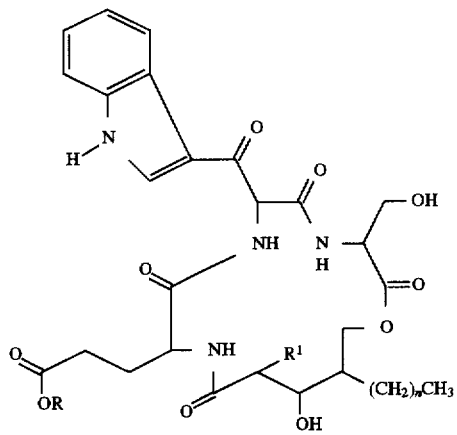

wherein n is 3 to 10;

R is hydrogen, $C_1-C_4$ alkyl or a pharmaceutically acceptable salt cation selected from the group consisting of sodium, potassium, calcium, lithium, magnesium, ammonium, and tetra($C_1-C_4$)alkyl ammonium; and $R^1$ is hydrogen or methyl.

9. The compound according to claim 8:

10. A fungicidal composition comprising an inert solid or liquid diluent and a fungicidally effective amount of the compound according to claim 8.

11. A process for producing an antifungal compound Formula I or II:

Formula I

Formula II wherein n is 3 to 10;

R is hydrogen, $C_1-C_4$ alkyl or a pharmaceutically acceptable salt cation selected from the group consisting of sodium, potassium, calcium, lithium, magnesium, ammonium and tetra($C_1-C_4$)alkyl ammonium;

$R^1$ is hydrogen or methyl; and $R^2$ is hydrogen or methyl;

which comprises aerobically fermenting the fungus *Hypoxylon oceanicum* LL-15G256 NRRL 21363 or mutants thereof which produce said antifungal compounds in a liquid medium containing assimilable sources of carbon, nitrogen and inorganic salts, until substantial antifungal activity is imparted to said medium and then recovering said antifungal compound therefrom.

12. The process according to claim 11 for producing an antifungal compound selected from the group consisting of LL-15G256g, LL-15G256d, LL-15G256e and LL-15G256g methyl ester.

13. A biologically pure culture of the fungus *Hypoxylon oceanicum* LL-15G256 NRRL 21363, or mutants thereof, said culture and said mutants being capable of producing antifungal compounds LL-15G256γ, LL-15G256δ and LL-15G256ε in recoverable quantities upon fermentation in an aqueous nutrient medium containing assimilable sources of carbon, nitrogen and inorganic salts.

14. A complex of antifungal compounds produced by aerobically fermenting fungal culture *Hypoxylon oceanicum* LL-15G256 NRRL 21363 in a liquid medium containing assimilable sources of carbon, nitrogen and inorganic salts, until substantial antifungal activity is imparted to said medium and then recovering said complex of antifungal compounds therefrom.

* * * * *